United States Patent [19]

Kushelvesky

[11] Patent Number: 5,668,743
[45] Date of Patent: Sep. 16, 1997

[54] METHOD FOR VISION TESTING

[75] Inventor: Avraham Kushelvesky, Metar, Israel

[73] Assignee: Optitest Ltd., Ofakim, Israel

[21] Appl. No.: 510,332

[22] Filed: Aug. 2, 1995

[30] Foreign Application Priority Data

Aug. 2, 1994 [IL] Israel ............................ 110547

[51] Int. Cl.⁶ .................................................. A01B 3/10
[52] U.S. Cl. ........................ 364/561; 73/597; 73/620; 351/200; 351/208; 351/210; 351/211; 351/243
[58] Field of Search ................................ 351/239, 243, 351/245, 200, 208, 210, 211; 364/561; 73/597, 620–624

[56] References Cited

U.S. PATENT DOCUMENTS

| | | | |
|---|---|---|---|
| 4,105,302 | 8/1978 | Tate, Jr. ............................... | 351/7 |
| 4,869,589 | 9/1989 | Blair et al. ........................... | 351/243 |
| 4,944,585 | 7/1990 | Mizuno ............................... | 351/204 |
| 4,976,149 | 12/1990 | Ichikawa et al. ................... | 73/597 |
| 5,140,859 | 8/1992 | Shah .................................. | 73/597 |
| 5,185,517 | 2/1993 | Inamori et al. .................... | 250/251.04 |
| 5,255,027 | 10/1993 | Reiner et al. ...................... | 351/211 |
| 5,515,853 | 5/1996 | Smith et al. ....................... | 128/661.01 |

OTHER PUBLICATIONS

"Measurements of Visual Acuity," by. C.A.P. Foxwell et al., *Brit J. of Ophthalmology* 1955.

*Primary Examiner*—Emanuel T. Voeltz
*Assistant Examiner*—Demetra R. Smith
*Attorney, Agent, or Firm*—Lowe, Price, LeBlanc & Becker

[57] ABSTRACT

A system and method are disclosed for vision testing wherein visual test patterns displayed on a computer display are adjusted according to predetermined criteria with the distance between the subject being tested and the test pattern being monitored by computer to achieve computer control and adjustment of test object size.

10 Claims, 1 Drawing Sheet

METHOD FOR VISION TESTING

FIELD OF THE INVENTION

The present invention relates to a method and to a system particularly useful for visual testing, using a computer. More specifically, the present invention relates to a method for adjusting visual test patterns automatically. Said method enables the computer to obtain the distance of a subject being tested (herein after called "the subject") from the test pattern on the computer display unit, thus enabling the computer to automatically adjust the size of the test object and other relevant parameters according to predetermined criteria, which depend on the said distance.

BACKGROUND OF THE INVENTION

Many of the vision tests, in particular tests which measure visual acuity, require the test objects to subtend an accurately prescribed angle on the retina (Foxell CAP et al, Measurement of Visual Acuity. Brit J. of Opthalmology 1955; 39:513-533). In the Snellen visual acuity test, for example, the visual angle of the test pattern (a letter, number etc.) is standardized to subtend 5 minutes of an arc with individual details of the object subtending 1 minute of an arc.

The visual angle is a function of 2 variables: the size of the object and its distance from the eye. Given an object of fixed size, the visual angle is inversely proportional to the distance of the object from the eye. And, vice versa, given a set distance between the object and the eye the visual angle is proportional to the size of the object. In many clinical tests the latter approach is used to achieve the required standard testing conditions. The distance at which the test pattern is viewed is stringently controlled, for example 20 feet for the Snellen chart, with the size of the test patterns is fixed accordingly. This approach is dictated by the fact that, once chosen, the size of the test patterns cannot be altered, and therfore only one specific distance fulfills the test criteria.

One drawback of this approach is that due to difficulties in maintaining the required distance, standardized conditions are not met and the test results are therefore not always reliable.

Using a computer to generate test patterns, removes the constraint of having to work with test patterns of fixed size, and therefore standardized conditions do not depend on conducting the test at a fixed distance, provided the computer is able to adjust the size of the test patterns according to the distance in order to meet the test criteria, or alternatively to make appropriate corrections when evaluating the results of the tests.

SUMMARY OF THE INVENTION

The present invention provides a method for automatically conveying to a computer the distance between the-subject and the test object on the computer display unit, particularly useful in vision testing characterized by the use of a distance measuring system interfaced with the computer.

The present invention relates furthermore to a system for automatically conveying to a computer the distance between the subject and the test object on the computer display unit, particularly useful in vision testing comprising of any distance measuring device, measuring the distance between the user and the computer, and said measuring device is interfaced with the computer.

DETAILED DESCRIPTION OF THE INVENTION

The distance measuring system can be any measuring distance system interfaced with the computer, such as a system based on ultrasonic, sound, electromagnetic, or an optical distance measurment device.

In a prefered embodiment of the present invention the distance between the subject and the computer display unit is measured using an automatic distance measuring device, consisting of a transmitter/receiver device, integrated into one unit, or seperated into two seperate units, located at the monitor, and an appropriate interface between the ouput of the distance measuring device and the input of the computer.

In a further prefered embodiment of the invention the computer instructs an electromagnetic transmitter to transmit an electromagnetic wave (hereby the trigger). Simultaneously the computer starts a timing measurment electronic circuits (herein after called "internal clock"). A receiver on the subject's body reacts virtually instantaneously to the signal from the trigger and activates an ultrasonic transmitter attached to the subject's body. This transmitter emits an ultrasonic signal back to an ultrasonic receiver interfaced to the computer and located at the monitor, stopping the operation of the internal clock. The time interval $\Delta t$, during which the internal clock is in operation, that is equal to the time it takes for the ultra sound signal to go from the subject's transmitter to the monitor, is used to calculate the distance d between the subject and the monitor, given the speed of ultra sound wave in air under given conditions v, according to the equation $d = v * \Delta t$.

If the initial triggering signal is also an ultra sound wave instead of being an electromagnetic signal, the distance is $d = (v * \Delta t)/2$, since the ultra sound signal takes double the time for the return trip.

The distance so calculated, is available to the computer for adjusting the size of the test image on the monitor automatically, according to preassigned criteria, or alternatively for applying an appropriate correction factor to the test results, using the unaltered test image.

Another possible application of the present invention is for adjusting the size of the image on the computer display, e.g. font size, to an optimum size, depending on the distance of the observer from the monitor. This is particularly useful for an observer suffering from presbyopia or other severe visual difficulties.

A further application of the automatic distance measurement method is for simultaneously testing the vision of a number of subjects. This is done by placing them at different distances from the monitor so that the system can identify each individual subject according to his position and interact with him on a time sharing basis, or by using a two dimensional vectorial distance detector interfaced with the computer as described bellow.

Another application of the invention is to place two receivers at the right angles to receive the ultra sound signal emitted by the transmitter on the subject. Since each of the detectors measures the distance of the subject in a different direction, the angular position of the subject with respect to the monitor may be calculated.

The present invention also relates to the use of an integrated ultra sound distance meter in which the electronic triggering and timing circuits, as well as the ultra sound transmitter and receiver, are contained in one package. Using this-arrangement the distance is calculated from the roundtrip time of the ultra sound wave reflected by the subject. As above, the information required for automatically adjusting the sizes of the visual test images is obtained by interfacing the output of the detector to the computer.

This latter method has the advantage of simplicity in that it does not require a transmitter to be placed on the subject.

But it is less sensitive because the reflected signal is weak and reflections from surrounding objects degrade the signal to noise ration interfering with the accuracy of the measurement.

An alternative method for measuring the distance of the subject from the test image monitor is by using an optical range finder, interfacing it's ouput to the computer. There are a number of optical range finding methods currently in use. However they are expensive, and in many cases, less accurate for short distances between 2–6 meters.

The present invention relates also to a method of testing the vision of a multiple number of subjects using test images on a single computer, as described above, so that the system can identify each individual subject according to his position and interact with him on a time sharing basis.

The present invention will be further described by FIGS. 1 and 2. These figures do not intend to limit the scope of the invention, but to illustrate and clarify it only.

Following is a detailed description of the figures:

Legend:

M—Monitor with test pattern.

$T_g$—Trigger $R_1$—Ultra sound receiver at the computer site $R_2$—A receiver attached to the subject.

$U_t$—Ultra sound transmitter.

S—Subject whose vision is to be tested.

D—Distance between monitor and subject.

C—Computer containing control and timing circuits.

Figure 1:
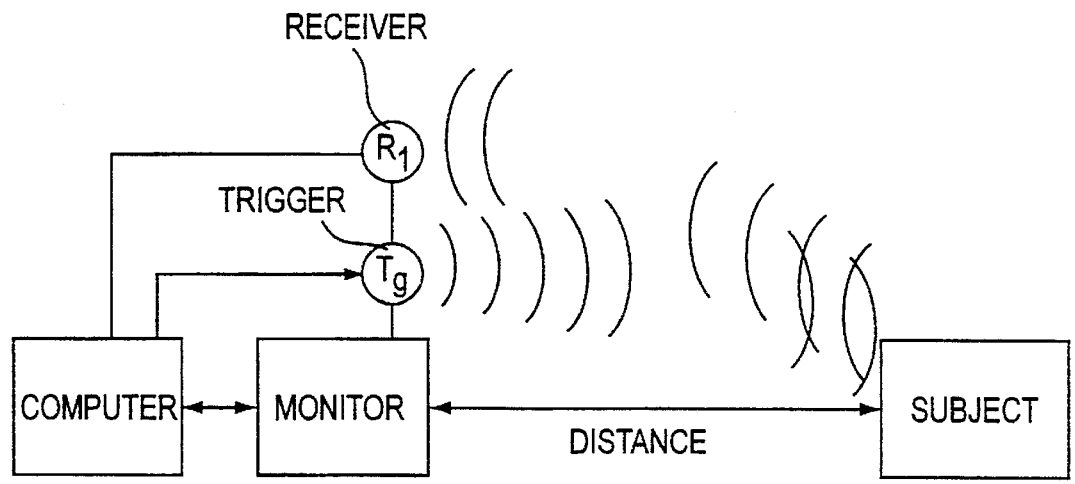
FIG. 1 is a block diagram of vision testing device measuring distance by using an optical distance meter.
Figure 2:
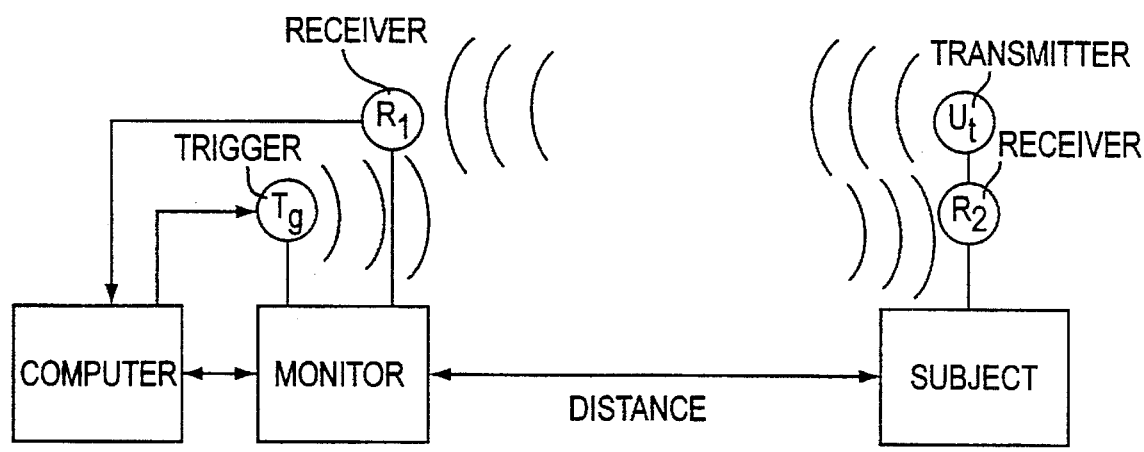
FIG. 2 shows the vision testing device of FIG. 1, with receiver/transmitter controlled by the computer and attached to the subject.

I claim:

1. A method for automatically conveying to a computerized system information a distance between a test image on a computer display unit and a subject viewing the same display unit, comprising the steps of automatically measuring the distance between the test image on a computer display unit and a subject viewing the same display unit and conveying the measured distance to said computerized system.

2. A method according to claim 1, wherein the automatic distance measuring system employs electromagnetic waves, or ultrsonic waves, or sound waves, or an optical range finder.

3. A method according to claim 1, wherein the distance measuring system consists of a first transmitter interfaced to and controlled by a computer; a first receiver attached to the computer display unit or at a fixed position in relation to it; and a second receiver/transmitter located on the subject or at a fixed distance related to the subject that picks up the signal emitted by the first transmitter, and in turn immediately triggers the subject's transmitter to emit a signal that is picked up by the computer interfaced receiver; and a time measuring circuit for measuring the time taken for the signal from the subject to reach the same first receiver; and a computing circuit for measuring the time interval to calculate the distance between the subject and the first receiver.

4. A method according to claim 3, using the measured distance to adjust the size of images on computer controlled display for visual testing according to preassigned criteria which depend on said distance.

5. A method according to claim 3, comprising the step of using the measured distance to correct the results of visual tests designed to be carried out at a standard distance which takes into account the actual distance measured.

6. A method to automatically obtain the distance of the subject from the computer display unit, in two or three dimensions, using two receivers or three detectors placed orthoganally to each other, and interfaced to a computer to receive the ultra sound signal emitted by the subject's transmitter as defined in claim 3, calculating the 2 or 3 vectorial distance of the subject to the computer display.

7. A method according to claim 3, using the measured distance to automatically adjust the size of the text on the computer display according to the actual distance measured.

8. A method according to claim 3, using the measured distance to acheive and maintain optimal visual conditions for viewing a text on the computer display.

9. A method for testing the vision of a multiple number of subjects using test images on a single computer display unit by using a vectorial distance measurement system as described in claim 6, so that the system can identify each individual subject according to said subject position and interact with said subject on a time sharing basis.

10. A system for automatically conveying to a computer a distance between the subject and a test object on a computer display unit for use in a vision testing system, comprising a measuring device interfaced with the computer, wherein the distance measuring device is comprised of a receiver/transmitter controlled by the computer; a receiver/transmitter unit attached to the subject's body; and electronic timing circuits interfaced to and controlled by the computer.

\* \* \* \* \*